United States Patent [19]

Loeffler et al.

[11] 4,213,976
[45] Jul. 22, 1980

[54] HALOALKYLDITHIOPHOSPHORIC ACID ESTERS

[75] Inventors: Hans-Peter Loeffler, Ludwigshafen; Heinrich Adolphi, Limburgerhof; Karl Kiehs, Lampertheim, all of Fed. Rep. of Germany

[73] Assignee: BASF Aktiengesellschaft, Fed. Rep. of Germany

[21] Appl. No.: 941,544

[22] Filed: Sep. 12, 1978

[30] Foreign Application Priority Data

Sep. 27, 1977 [DE] Fed. Rep. of Germany ....... 2743349

[51] Int. Cl.$^2$ .......................... A01N 9/36; C07F 9/165
[52] U.S. Cl. ...................................... 424/224; 260/963
[58] Field of Search .......................... 260/963; 424/224

[56] References Cited

U.S. PATENT DOCUMENTS

| | | | |
|---|---|---|---|
| 2,928,863 | 4/1960 | Schrader | 260/963 OR |
| 3,825,633 | 7/1974 | Tsuchiya et al. | 260/963 X |

FOREIGN PATENT DOCUMENTS

| | | | |
|---|---|---|---|
| 98101 | 2/1964 | Denmark | 260/963 |
| 1258922 | 12/1971 | United Kingdom | 260/963 |

*Primary Examiner*—Anton H. Sutto
*Attorney, Agent, or Firm*—Keil & Witherspoon

[57] ABSTRACT

Haloalkyldithiophosphoric acid esters of the formula

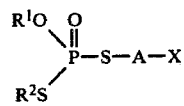

where $R^1$ is methyl or ethyl, $R^2$ is alkyl of 2 to 4 carbon atoms, A is linear or branched alkylene of 2 to 4 carbon atoms and X is chlorine or bromine, which are active against pests, especially insects, mites and ticks, a process for the manufacture of these active ingredients, pesticides containing these haloalkyldithiophosphoric acid esters as active ingredients, and a process for combating pests with these active ingredients.

7 Claims, No Drawings

HALOALKYLDITHIOPHOSPHORIC ACID ESTERS

The present invention relates to new haloalkyldithiophosphoric acid esters, a process for their manufacture and pesticides which contain these haloalkyldithiophosphoric acid esters as active ingredients.

U.S. Pat. No. 3,825,633 discloses that O-alkyl-S-alkyl-S-haloalkyl-bis-thiolphosphates act as insecticides. However, only those bis-thiolphosphates which, in addition to S-haloalkyl groups, contain S-phenylalkyl groups, eg. S-benzyl, S-1-phenylethyl, S-2-phenylethyl or S-3-phenylpropyl, as ester groups are described as active compounds.

We have found, surprisingly, that bis-thiolphosphates in which these phenyl-substituted alkyl groups are replaced by linear or branched unsubstituted alkyl groups have a substantially greater biological activity than the compounds known from U.S. Pat. No. 3,825,633. In particular, they may be used for combating harmful and troublesome insects, mites and ticks.

The haloalkyldithiophosphoric acid esters of the invention have the formula I

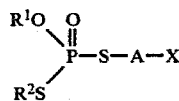

where $R^1$ is methyl or ethyl, $R^2$ is alkyl of 2 to 4 carbon atoms, A is unbranched or branched alkylene of 2 to 4 carbon atoms and X is chlorine or bromine.

The new haloalkyldithiophosphoric acid esters of the formula I are obtained by reacting a dithiophosphoric acid ester of the formula II

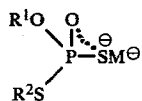

where $R^1$ and $R^2$ have the above meanings and $M^{\oplus}$ is an alkali metal ion, one equivalent of an alkaline earth metal ion or a substituted or unsubstituted ammonium ion, with a haloalkane of the formula III

Y—A—X where A and X have the above meanings and Y is halogen or another easily replaceable radical, in a solvent or diluent.

Examples, other than halogen, of easily replaceable radicals Y are sulfonate radicals, eg. the tosylate radical.

Suitable cations $M^{\oplus}$ are alkali metal ions, eg. sodium and potassium, alkaline earth metal ions, eg. calcium and magnesium, the ammonium ion and substituted ammonium ions, eg. alkylammonium, dialkylammonium and trialkylammonium ions.

The reaction is in general carried out in solvents or diluents which are inert toward the reactants. Examples of suitable materials are ketones, eg. acetone, methyl ethyl ketone and diethyl ketone, aromatic hydrocarbons, eg. toluene and xylenes, nitriles, eg. acetonitrile, esters, eg. ethyl acetate, and dimethylformamide.

The reaction can be carried out in a two-phase system of water and the haloalkane as the second phase. Reaction accelerators, eg. small amounts of dimethylformamide, may also be added to the reaction mixture.

The reaction temperature depends on the reactivity of the haloalkane and may be varied within a substantial range. Advantageously, the reaction is carried out at from 30° to 100° C.

The starting materials may be employed in the equimolar ratio. However, it may be necessary to employ an excess of the haloalkane, with the degree of excess depending on the relative ease of replacement of the substituents X and Y in the haloalkane and on the mobility of the halogen atom X in the end product. Unconverted haloalkane can be recovered at the end of the reaction.

The starting compounds of the formulae II and III are known and can be prepared by conventional methods.

Compounds of the formula I, where $R^1$, $R^2$ and X have the above meanings, and A is —(CH$_2$)$_2$—, may also be prepared by an addition reaction of a sulfenyl halide with ethylene, in accordance with the following equation:

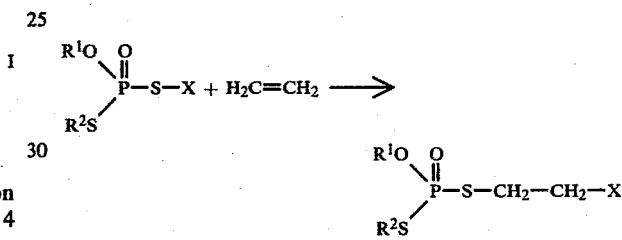

These compounds may also be obtained by reacting a phosphoryl halide with ethylene sulfide in accordance with the following equation:

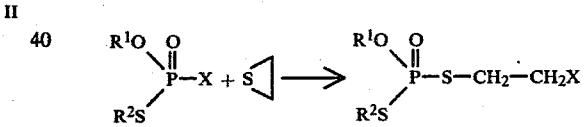

In a further method of synthesis of these compounds, the starting material is the known phospholane IV, which reacts with the sulfenyl halide $R^2$—S—X, in a reaction which in principle has been disclosed, with ring opening and formation of V. The latter can be converted to the desired end product by means of sodium ethanolate or sodium methanolate.

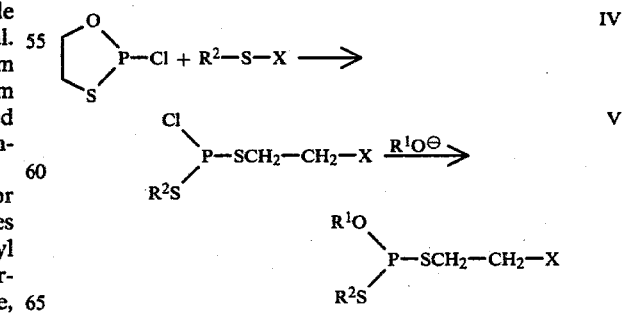

The Examples which follow illustrate the preparation of the novel compounds:

1. Preparation of S-2-bromoethyl-S-n-propyl-O-ethyl-bisthiolphosphate

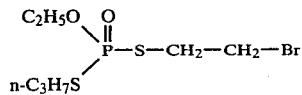

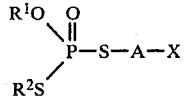

can be prepared by a similar method:

| No. | $R^1$ | $R^2$ | A | X | Physical data | |
|---|---|---|---|---|---|---|
| 1 | $C_2H_5$ | n-$C_3H_7$ | —$(CH_2)_2$— | Br | $n_D^{24}$ | 1.5402 |
| 2 | $C_2H_5$ | i-$C_3H_7$ | —$(CH_2)_2$— | Br | $n_D^{23}$ | 1.5375 |
| 3 | $C_2H_5$ | n-$C_3H_7$ | —$(CH_2)_3$— | Cl | $n_D^{23}$ | 1.5180 |
| 4 | $C_2H_5$ | n-$C_3H_7$ | —$(CH_2)_2$— | Cl | $n_D^{28}$ | 1.5192 |
| 5 | $C_2H_5$ | n-$C_3H_7$ | —$(CH_2)_3$— | Br | $n_D^{31}$ | 1.5289 |
| 6 | $C_2H_5$ | n-$C_3H_7$ | —$CH_2$—$CH(CH_3)$—$CH_2$— | Cl | $n_D^{22}$ | 1.5112 |
| 7 | $C_2H_5$ | n-$C_3H_7$ | —$CH_2$—$CH(CH_3)$— | Br | $n_D^{29}$ | 1.5240 |
| 8 | $C_2H_5$ | sec.-$C_4H_9$ | —$(CH_2)_2$— | Br | $n_D^{25}$ | 1.5278 |
| 9 | $C_2H_5$ | sec.-$C_4H_9$ | —$(CH_2)_2$13 | Cl | $n_D^{23}$ | 1.5170 |
| 10 | $C_2H_5$ | sec.-$C_4H_9$ | —$(CH_2)_3$— | Br | $n_D^{24}$ | 1.5258 |
| 11 | $C_2H_5$ | sec.-$C_4H_9$ | —$(CH_2)_3$— | Cl | $n_D^{23}$ | 1.5152 |
| 12 | $C_2H_5$ | i-$C_3H_7$ | —$(CH_2)_2$— | Cl | | |
| 13 | $C_2H_5$ | i-$C_3H_7$ | —$(CH_2)_3$— | Br | | |
| 14 | $C_2H_5$ | i-$C_3H_7$ | —$(CH_2)_3$— | Cl | | |
| 15 | $C_2H_5$ | i-$C_4H_9$ | —$(CH_2)_2$— | Br | $n_D^{28}$ | 1.5312 |
| 16 | $C_2H_5$ | n-$C_4H_9$ | —$(CH_2)_2$— | Cl | $n_D^{31}$ | 1.5134 |
| 17 | $C_2H_5$ | n-$C_4H_9$ | $(CH_2)_3$— | Br | $n_D^{33}$ | 1.5183 |
| 18 | $C_2H_5$ | n-$C_4H_9$ | —$(CH_2)_3$— | Cl | $n_D^{24}$ | 1.5149 |
| 19 | $C_2H_5$ | i-$C_4H_9$ | —$(CH_2)_2$— | Br | $n_D^{27}$ | 1.5281 |
| 20 | $C_2H_5$ | i-$C_4H_9$ | —$(CH_2)_2$— | Cl | $n_D^{26}$ | 1.5103 |
| 21 | $C_2H_5$ | i-$C_4H_9$ | —$(CH_2)_3$— | Br | $n_D^{23}$ | 1.5276 |
| 22 | $C_2H_5$ | i-$C_4H_9$ | —$(CH_2)_3$— | Cl | $n_D^{32}$ | 1.5092 |
| 23 | $CH_3$ | n-$C_3H_7$ | —$(CH_2)_2$— | Br | | |
| 24 | $C_2H_5$ | $C_2H_5$ | —$(CH_2)_2$— | Br | $n_D^{21}$ | 1.5462 |
| 25 | $C_2H_5$ | $C_2H_5$ | —$(CH_2)_2$— | Cl | $n_D^{24}$ | 1.5289 |
| 26 | $C_2H_5$ | $C_2H_5$ | —$(CH_2)_3$— | Br | $n_D^{28}$ | 1.5359 |
| 27 | $C_2H_5$ | $C_2H_5$ | —$(CH_2)_3$— | Cl | | |
| 28 | $C_2H_5$ | n-$C_3H_7$ | —$(CH_2)_4$— | Br | $n_D^{23}$ | 1.5300 |
| 29 | $C_2H_5$ | n-$C_3H_7$ | —$(CH_2)_4$— | Cl | $n_D^{27}$ | 1.5122 |

166.5 g of potassium O-ethyl-S-n-propyl-dithiophosphate are added in portions to 525 g of 1,2-dibromoethane in 500 ml of acetonitrile at 80° C. in the course of 3 hours, whilst stirring. The mixture is stirred for a further 2 hours at 80° C. and is then filtered, and the solvent and excess 1,2-dibromoethane are distilled off. The residue is taken up in 800 ml of methylene chloride and this solution is washed four times with water and dried over sodium sulfate. After stripping off the solvent, volatile impurities are removed from the residue at 70° C./0.05 mm Hg. 108 g of end product are obtained; $n_D^{24} = 1.5402$.

2. Preparation of S-2-chloroethyl-S-n-propyl-O-ethyl-bisthiolphosphate

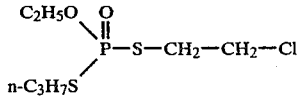

17.2 g of N,N-dimethylammonium O-ethyl-S-n-propyldithiophosphate, 50 ml of water, 28.6 g of 1-bromo-2-chloroethane and 2 ml of N,N-dimethylformamide are heated for 12 hours at 60° C. After the mixture has cooled, 300 ml of chloroform are added. This mixture is washed three times with water, dried and concentrated. 7 g of a pale yellow oil are obtained; $n_D^{28} = 1.5192$.

The following compounds of the formula I

The novel haloalkyldithiophosphoric acid esters may be used for combating pests from the order of the butterflies (Lepidoptera), eg. *Plutella maculipennis, Leucoptera coffeella, Hyponomeuta malinellus, Argyresthia conjegella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia keuhniella, Chilo suppressalis, Calleria mellonella, Malacosoma neustria, Dendrolimus pini, Thaumatopoea pityocampa, Phalera bucephala, Cheimatobia brumata, Hibernia defoliaria, Bupalus piniarius, Hyphantria cunea, Agrotis segetum, Agrotis ypsilon, Barathra brassicae, Cirphis unipuncta, Prodenia litura, Laphygma exigua Panolis flammea, Earias insulana, Plusia gamma, Alabama argillacea, Lymantria dispar, Lymantria Monacha, Pieris brassicae* and *Aporia crataegi;* from the order of the beetles (Coleoptera), eg. *Blitophaga undata, Melanotus communis, Limonius californicus, Agriotes lineatus, Agriotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleriae, Phyllotreta nemorum, Chaetocnema tibialis, Psylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abieties, Byctiscus betulae, Anthonomus pomorum, Anthonomus grandis, Ceuthorrhyn-* chus assimilis, Ceuthorrhynchus napi, Sitophilus granaria, Anisandrus dispar, Ips typographus and Blastophagus piniperda; from the order of the diptera, eg. Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae and Pegomya hyoscyami; from the order of the hymenoptera, eg. Athalia rosae, Hoplocampa minuta, Monomorium pharaonis, Solenopsis geminata and Atta sexdens; from the order of the bugs (Heteroptera), eg. Nezara viridula, Eurygaster integriceps, Blissus leucopterus, Dysdercus cingulatus, Piesma quadrata, and Lygus pratensis; from the order of the homoptera, eg. Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Eriosoma lanigerum, Pemphigus bursarius, Dreyfusia nordmannianae, Dreyfusia piceae, Adelges laricis and Viteus vitifolii; from the order of the termites (Isoptera), eg. Reticulitermes lucifugus; as well as for combating the mites and ticks belonging to the order of the Arachnoidea (Acarina), eg. Tetranychus urticae, Tetranychus atlanticus, Tetranychus pacificus, Paratetranychus pilosus, Byrobia praetiosa, Ixodes ricinus, Ornithodorus moubata, Ablyomma americanum, Dermacentor silvarum and Boophilus microplus.

The compounds according to the invention can be employed successfully as pesticides in crop protection, as well as in the hygiene sector, the protection of stored products and the veterinary sector, by allowing them to act on the pests or their habitat.

Particularly active compounds of the formula I are those where A is the ethylene radical, and more particularly those where, furthermore, $R^1$ is ethyl and $R^2$ is propyl, especially n-propyl.

The active ingredients may be applied as such, as their formulations, or as the forms for application, prepared therefrom, eg. in the form of directly sprayable solutions, powders, suspensions, dispersions, emulsions, oil dispersions, pastes, dusts, broadcasting agents or granules, by spraying, atomizing, dusting, broadcasting or watering. The form for application depends entirely on the intended use but should in every case ensure very fine distribution of the active ingredients of the invention.

For the preparation of directly sprayable solutions, emulsions, pastes and oil dispersions, it is possible to use mineral oil fractions of medium to high boiling point, eg. kerosene or diesel oil, coal tar oils and oils of vegetable or animal origin, aliphatic, cycloaliphatic and aromatic hydrocarbons, eg. benzene, toluene, xylene, paraffin, tetrahydronaphthalene and alkylated naphthalenes, or derivatives of these, eg. methanol, ethanol, propanol, butanol, chloroform, carbon tetrachloride, cyclohexanol, cyclohexanone, chlorobenzene and isophorone, and strongly polar solvents, eg. dimethylformamide, dimethylsulfoxide, N-methylpyrrolidone and water.

Aqueous forms for application may be prepared from emulsion concentrates, pastes, wettable powders or oil dispersions by adding water. To prepare emulsions, pastes or oil dispersions the ingredients as such, or dissolved in an oil or solvent, may be homogenized in water by means of wetting agents, adhesives, dispersants or emulsifiers. However, it is also possible to prepare concentrates, suitable for dilution with water, from the active ingredient, wetting agent, adhesive, dispersant or emulsifier, with or without a solvent or oil.

Examples of surfactants are alkali metal, alkaline earth metal and ammonium salts of ligninsulfonic acid, naphthalenesulfonic acid and phenolsulfonic acids, alkylarylsulfonates, alkyl-sulfates, alkylsulfonates, alkali metal salts and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensation products of sulfonated naphthalene and naphthalene derivatives with formaldehyde, condensation products of naphthalene or of naphthalenesulfonic acids with phenol and formaldehyde, polyoxyethylene octylphenol ether, oxyethylated isooctylphenol, octylphenol and nonylphenol, alkylphenol polyglycol ethers, tributylphenyl polyglycol ethers, alkylaryl polyether-alcohols, isotridecyl alcohol, ethylene oxide condensates with fatty alcohols, oxyethylated castor oil, oxyethylated polyoxypropylene, lauryl alcohol polyglycol ether acetal, sorbitol esters, lignin, sulfite waste liquors and methylcellulose.

Powders, broadcasting agents and dusts may be prepared by mixing or grinding the active ingredients with a solid carrier.

Granules, eg. coated, impregnated and homogeneous granules, can be prepared by binding the active ingredients to solid carriers. Examples of solid carriers are mineral earths, eg. silica gel, silicic acids, silicates, talc, kaolin, attaclay, limestone, lime, chalk, bole, loess, clay, dolomite, diatomaceous earth, calcium sulfate, magnesium sulfate, magnesium oxide, ground plastics, fertilizers, eg. ammonium sulfate, ammonium phosphate, ammonium nitrate and ureas, and vegetable products, eg. cereal flours, bark meal, wood flour and nutshell flour, cellulose powders and other solid carriers.

The formulations in general contain from 0.1 to 95% by weight, preferably from 0.5 to 90% by weight, of active ingredient.

The concentrations of active ingredient in the ready-to-use formulations may be varied within a substantial range. In general, they are from 0.0001 to 10%, preferably from 0.01 to 1%.

The active ingredients may also be employed successfully in the ultra-low volume process (ULV) where it is possible to apply formulations containing more than 95% by weight of active ingredient or even the 100% strength active ingredient alone.

The following are examples of suitable formulations.

1.

250 g of active ingredient (eg. S-2-bromoethyl-S-n-propyl-O-ethyl-bis-thiolphosphate)
15 g of calcium dodecylbenzenesulfonate
35 g of oxyethylated castor oil
50 g of oxyethylated nonylphenol
xylene to make up to 1,000 ml.

2.

20 parts of S-2-chloroethyl-S-n-propyl-O-ethyl-bis-thiolphosphate are intimately mixed with 2 parts of calcium dodecylbenzenesulfonate, 8 parts of a fatty alcohol polyglycol ether, 2 parts of the sodium salt of a phenolsulfonic acid/urea/formaldehyde condensate and 68 parts of a paraffinic mineral oil. A stable oily dispersion is obtained.

3.

3 parts by weight of S-3-chloro-n-propyl-S-n-propyl-O-ethyl-bis-thiolphosphate are intimately mixed with 97 parts by weight of finely divided kaolin. A dust containing 3% by weight of active ingredient is obtained.

4.

20 parts by weight of S-3-chloro-n-propyl-S-sec.-butyl-O-ethyl-bis-thiolphosphate are dissolved in a mixture comprising 40 parts by weight of cyclohexanone, 30 parts by weight of isobutanol, 20 parts by weight of an adduct of 7 moles of ethylene oxide with 1 mole of isooctylphenol and 10 parts by weight of an adduct of 40 moles of ethylene oxide with 1 mole of castor oil. The solution is poured into 100,000 parts by weight of water and finely dispersed therein, giving an aqueous dispersion containing 0.01% by weight of the active ingredient.

To the individual active ingredients or their mixtures there may be added (if desired only immediately before use (tank-mix)), oils of various types, herbicides, fungicides, bactericides and other insecticides. These agents may be added to the agents of the invention in a weight ratio of from 1:10 to 10:1.

The following are examples of agents which may thus be added: 1,2-dibromo-3-chloropropane, 1,3-dichloropropene, 1,3-dichloropropene + 1,2-dichloropropane, 1,2-dibromoethane, 2-sec.-butylphenyl N-methylcarbamate, o-chlorophenyl N-methylcarbamate, 3-isopropyl-5-methyl-phenyl N-methylcarbamate, o-isopropoxyphenyl N-methylcarbamate, 3,5-dimethyl-4-methylmercaptophenyl N-methylcarbamate, 4-dimethylamino-3,5-xylyl N-methylcarbamate, 2-(1,3-dioxolan-2-yl)-phenyl-N-methylcarbamate, 1-naphthyl N-methylcarbamate, 2,3-dihydro-2,2-dimethylbenzofuran-7-yl N-methylcarbamate, 2,2-dimethyl-1,3-benzodioxol-4-yl N-methylcarbamate, 2-dimethylamino-5,6-dimethyl-pyrimidin-4-yl dimethylcarbamate, 2-methyl-2-(methylthio)-propionaldehyde-O-(methylcarbamyl)-oxime, S-methyl-N-(methylcarbamyloxy)-thioacetimidate, methyl-N',N'-dimethyl-N-(methylcarbamyloxy)-1-thiooxamidate, N-(2-methyl-4-chlorophenyl)-N',N'-dimethylformamidine, tetrachlorothiophene, O,O-dimethyl-O-(p-nitrophenyl)-phosphorothioate, O,O-diethyl-O-(p-nitrophenyl)phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenyl-phosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropyl-phosphoroamidate, O,O-diethyl-O-[p-(methylsulfinyl)-phenyl]-phosphorothioate, O-ethyl-S-phenyl-ethyl-phosphonothioate, O,O-diethyl-[2-chloro-1-(2,4-dichlorophenyl)-vinyl]-phosphate, O,O-dimethyl-[2-chloro-1-(2,4,5-trichlorophenyl)]-vinyl-phosphate, O,O-dimethyl-S-(α-ethoxycarbonylbenzyl)-phosphorodithioate, bis-(dimethylamino)-fluoro-phosphine oxide, octamethyl-pyrophosphoramide, O,O,O,O-tetraethyl-dithio-pyrophosphate, S-chloromethyl-O,O-diethyl-phosphorodithioate, O-ethyl-S,S-dipropyl-phosphorodithioate, O,O-dimethyl-O-2,2-dichlorovinyl-phosphate, O,O-dimethyl-1,2-dibromo-2,2-dichloroethylphosphate, O,O-dimethyl-2,2,2-trichloro-1-hydroxy-ethylphosphonate, O,O-dimethyl-S-[1,2-bis-carboethoxy-ethyl-(1)]-phosphorodithioate, O,O-dimethyl-O-(1-methyl-2-carbomethoxyvinyl)-phosphate, O,O-dimethyl-S-(N-methyl-carbamyl-methyl)-phosphorodithioate, O,O-dimethyl-S-(N-methyl-carbamylmethyl)-phosphorothioate, O,O-dimethyl-S-(N-methoxyethylcarbamyl-methyl)-phosphorodithioate, O,O-dimethyl-S-(N-formyl-N-methyl-carbamylmethyl)-phosphorodithioate, O,O-dimethyl-O-[1-methyl-2-(methyl-carbamyl)-vinyl]-phosphate, O,O-dimethyl-O-[(1-methyl-2-dimethylcarbamyl)-vinyl]-phosphate, O,O-dimethyl-O-[(1-methyl-2-chloro-2-diethyl-carbamyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethyl-S-(2-ethylsulfinylethyl)-phosphorothioate, O,O-diethyl-S-(2-ethylthioethyl)-phosphorodithioate, O,O-dimethyl-S-(2-ethylsulfinylethyl)-phosphorothioate, O,O-diethyl-thiophosphoryl-iminophenyl-acetonitrile, O,O-diethyl-S-(2-chloro-1-phthalimidoethyl)-phosphorodithioate, O,O-diethyl-S-(6-chloro-benzoxazol-2-on-3-yl)-methyldithiophosphate, O,O-dimethyl-S-(2-methoxy-1,3,4-thiadiazol-5-on-4-yl-methyl)-phosphorodithioate, O,O-diethyl-O-(3,5,6-trichloro-pyrid-2-yl)-phosphorothioate, O,O-diethyl-O-(2-pyrazinyl)-phosphorothioate, O,O-diethyl-O-(2-isopropyl-4-methyl-pyrimidin-6-yl)-phosphorothioate, O,O-diethyl-O-(2-diethylamino-6-methyl-4-pyrimidinyl)-thionophosphate, O,O-dimethyl-S-(4-oxo-1,2,3-benzotriazin-3-yl-methyl)-phosphorodithioate, O,O-dimethyl-S-(4,6-diamino-1,3,5-triazin-2-yl-methyl)-phosphorodithioate, O,O-diethyl-(1-phenyl-1,2,4-triazol-3-yl)-thionophosphate, O,S-dimethyl-phosphoramidothioate, O,S-dimethyl-N-acetyl-phosphroamidothioate, γ-hexachlorocyclohexane, 1,1-di-(p-methoxyphenyl)-2,2,2-trichloroethane and 6,7,8,9,10,10-hexachloro-1,5,5a,6,9,9a-hexahydro-6,9-methano-2,4,3-benzodioxathiepin-3-oxide.

The Examples which follow demonstrate the biological action. Comparisons were carried out with O,O-dimethyl-O-[(1-methyl-2-chloro-2-diethyl-carbamyl)-vinyl]-phosphate (Belgian Pat. No. 552,284; No. I), S-benzyl-S-2-chloroethyl-O-ethyl-bis-thiol-phosphate (U.S. Pat. No. 3,825,633, No. II), S-2-bromoethyl-O,O-diethyl-phosphorodithioate (German Published Application DAS 1,005,058; No. III) and S-chloromethyl-O,O-diethyl-phosphorodithioate (German Laid-Open Application DOS 1,925,468; No. IV).

EXAMPLE A

Contact action on cockroaches (*Blatta orientalis*)

The bottom of a 1 liter beaker is treated with a solution of the active ingredient in acetone. After the solvent has evaporated, 5 adult cockroaches are introduced into each beaker. The mortality rate is determined after 48 hours.

| Active ingredient No. | Amount of active ingredient per beaker [mg] | Mortality rate [%] |
| --- | --- | --- |
| 1 | 0.2 | 100 |
|   | 0.1 | 80 |
| 2 | 0.2 | 100 |
|   | 0.1 | 80 |
| 3 | 0.2 | 100 |
| 4 | 0.1 | 100 |
| 6 | 0.2 | 100 |
|   | 0.1 | 80 |
| 7 | 0.2 | 100 |
| 8 | 0.05 | 100 |
| 9 | 0.2 | 100 |
| 10 | 0.2 | 100 |
| 11 | 0.1 | 100 |
| I | 0.1 | 40 |
| II | 0.5 | 80 |
| III | 1.0 | 80 |

EXAMPLE B

Contact action on house flies (*Musca domestica*); prolonged contact

Both parts of a Petri dish of 10 cm diameter are lined with a total of 2 ml of the solution of the active ingredient in acetone. After the solvent has evaporated (in about 30 minutes), 10 flies are introduced into each dish. The mortality rate is determined after 4 hours.

| Active ingredient No. | Amount of active ingredient [mg] | Mortality rate [%] |
| --- | --- | --- |
| 2 | 0.2 | 100 |
| 3 | 0.02 | 80 |
| 4 | 0.005 | 80 |
| 6 | 0.2 | 100 |
| 7 | 0.02 | 100 |
| 8 | 0.04 | 80 |
| 9 | 0.01 | 100 |
| 10 | 0.02 | 100 |
| 11 | 0.005 | 80 |
| I | 0.5 | 100 |
|   | 0.2 | 20 |
| II | 2.0 | 50 |

EXAMPLE C

Breeding experiment with *Drosophila melanogaster*

40 ml of a bran/agar nutrient are introduced into 250 ml plastic bottles at 50° C. and then mixed intimately with 2 ml of the aqueous formulation of active ingredient.

When the nutrient has cooled, it is inoculated with a yeast suspension, and a rolled filter paper is introduced. From 20 to 40 Drosophila, about 6 days old, are then placed in the vessel and the latter is closed.

The results are evaluated after 10 days.

| Active ingredient No. | Concentration of the active ingredient formulation [ppm] |   |
| --- | --- | --- |
| 1 | 5 | development inhibited |
| 3 | 5 | development inhibited |
| 4 | 5 | development inhibited |
| 5 | 5 | development inhibited |
| 6 | 5 | development inhibited |
| 7 | 5 | development inhibited |
| 8 | 2.5 | development inhibited |
| 9 | 1.0 | development inhibited |
| 10 | 2.5 | development inhibited |
| 11 | 2.5 | development inhibited |
| I | 25 | development inhibited |
|   | 10 | inactive |

EXAMPLE D

Contact action on granary weevils (*Sitophilus granaria*).

Petri dishes of 10 cm diameter are lined with solutions of active ingredient in acetone. When the solvent has evaporated, 100 granary weevils are placed in each dish. After 4 hours, the weevils are introduced into untreated papier mâché dishes and the number of animals still capable of leaving these dishes is observed.

| Active ingredient No. | Amount of active ingredient per dish [mg] | Mortality rate [%] |
| --- | --- | --- |
| 1 | 0.1 | 100 |
| 3 | 0.1 | 100 |
| 4 | 0.1 | 80 |
| 5 | 0.1 | 80 |
| 6 | 0.1 | 100 |
| 7 | 0.1 | 100 |
| 8 | 0.02 | 100 |
| 9 | 0.2 | 100 |
| 10 | 0.05 | 80 |
| 11 | 0.05 | 80 |
| I | 1.0 | 100 |
|   | 0.2 | inactive |
| III | 0.2 | inactive |
| IV | 0.2 | inactive |

EXAMPLE E

Contact action on Malathion-resistant red flour beetle (*Tribolium castaneum*)

Red flour beetles are exposed for 24 hours on filter paper discs (diameter 7 cm) treated with a solution of the active ingredient in acetone, within glass rings of 4.5 cm diameter.

| Active ingredient No. | Amount of active ingredient per filter paper disc [mg] | Mortality rate [%] |
| --- | --- | --- |
| 1 | 0.25 | 100 |
| 2 | 0.12 | 100 |
| 3 | 0.25 | 100 |
| 6 | 0.25 | 100 |
| I | 0.5 | 100 |
|   | 0.25 | 40 |

EXAMPLE F

Breeding experiment with house flies (*Musca domestica*)

50 g of a nutrient medium comprising 100 parts of water, 10 parts of baker's yeast, 10 parts of dried milk and 1 part of agar are thoroughly mixed, whilst warm, with an aqueous formulation of the active ingredient. When the nutrient medium has cooled, about 0.1 ml of fly eggs is placed thereon and the development of the eggs is observed over one week. The experiment is carried out at 20° C.

| Active ingredient No. | Minimum active ingredient concentration of the formulation [ppm], at which development is inhibited |
|---|---|
| 1 | 1 |
| I | 10 |

We claim:

1. A haloalkyldithiophosphoric acid ester of the formula I

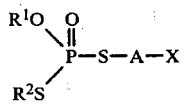

where $R^1$ is methyl or ethyl, $R^2$ is alkyl of 2 to 4 carbon atoms, A is linear or branched alkylene of 2 to 4 carbon atoms and X is chlorine or bromine.

2. S-2-Chloroethyl-S-n-propyl-O-ethyl-bis-thiolphosphate.

3. S-2-Bromoethyl-S-n-propyl-O-ethyl-bis-thiolphosphate.

4. A pesticide containing a solid or liquid inert carrier and one or more haloalkyldithiophosphoric acid esters of the formula I.

5. A process of pest control, wherein a haloalkyldithiophosphoric acid ester of the formula I is allowed to act on the pests or their habitat.

6. S-2-chloroethyl-S-sec-butyl-O-ethyl-bisthiolphosphate.

7. S-2-bromoethyl-S-sec-butyl-O-ethyl-bisthiolphosphate.